US012708645B2

(12) United States Patent
Prendergast et al.

(10) Patent No.: US 12,708,645 B2
(45) Date of Patent: Aug. 18, 2026

(54) TOPICAL PREPARATIONS

(71) Applicant: Epitheal Limited, Galway (IE)

(72) Inventors: John Patrick Prendergast, Galway (IE); Michael Joseph Mcloughlin, Galway (IE)

(73) Assignee: EPITHEAL LIMITED, Galway (IE)

( * ) Notice: Subject to any disclaimer, the term of this patent is extended or adjusted under 35 U.S.C. 154(b) by 729 days.

(21) Appl. No.: 17/911,033

(22) PCT Filed: Mar. 11, 2021

(86) PCT No.: PCT/EP2021/056268
§ 371 (c)(1),
(2) Date: Sep. 12, 2022

(87) PCT Pub. No.: WO2021/180896
PCT Pub. Date: Sep. 16, 2021

(65) Prior Publication Data

US 2023/0190792 A1 Jun. 22, 2023

(30) Foreign Application Priority Data

Mar. 13, 2020 (GB) ...................................... 2003666

(51) Int. Cl.

| | |
|---|---|
| ***A61K 33/30*** | (2006.01) |
| ***A61K 9/00*** | (2006.01) |
| ***A61K 31/60*** | (2006.01) |
| ***A61K 33/18*** | (2006.01) |
| ***A61P 17/00*** | (2006.01) |

(52) U.S. Cl.
CPC ............ *A61K 33/30* (2013.01); *A61K 9/0014* (2013.01); *A61K 31/60* (2013.01); *A61K 33/18* (2013.01); *A61P 17/00* (2018.01); *A61K 2300/00* (2013.01)

(58) Field of Classification Search
CPC ........ A61K 33/30; A61K 33/18; A61K 31/60; A61K 2300/00
See application file for complete search history.

(56) References Cited

U.S. PATENT DOCUMENTS

2011/0038965 A1* 2/2011 McKay .................. A61K 45/06 514/25
2017/0172879 A1* 6/2017 Ragoonath ............... A61K 8/27

FOREIGN PATENT DOCUMENTS

| | | | | | |
|---|---|---|---|---|---|
| DE | 102015013885 | A1 | | 5/2017 | |
| EP | 3072509 | A1 | * | 9/2016 | ........... A61K 36/185 |
| GB | 981144 | A | * | 1/1965 | ............. A61K 31/60 |
| UA | 6791 | A | | 12/1994 | |
| WO | 2016134130 | A1 | | 8/2016 | |
| WO | WO-2019023685 | A1 | * | 1/2019 | ........... A61L 29/085 |

OTHER PUBLICATIONS

Foodcircle, (Plant-Based Fats and Oils in Soaps, Downloaded Jun. 2025, https://www.foodcircle.com/magazine/plant-oils-fats-saponification-soaps?locale=de)) (Year: 2025).*
Yeasmin et al (International Journal of Molecular Sciences, 2020, vol. 21, pp. 9049) (Year: 2020).*
Noulas (Journal of Trace Elements in Medicine and Biology, 2018) (Year: 2018).*
Kiferle et al (bioRxiv, 2020, https://doi.org/10.1101/2020.09.16.300079, pp. 1-46) (Year: 2020).*
Search and Examination Report dated Aug. 28, 2020 pertaining to GB Application No. 2003666.1 filed Mar. 13, 2020, pp. 1-9.

* cited by examiner

*Primary Examiner* — Mark V Stevens
(74) *Attorney, Agent, or Firm* — DINSMORE & SHOHL LLP

(57) ABSTRACT

A topical preparation for use in treating dermatological ailments is prepared from a mixture comprising salicylic acid or a salt thereof, zinc or a salt thereof, iodine or a salt thereof, and a pharmaceutically acceptable carrier vehicle. The preparation comprises any one or more of anti-inflammatory properties, keratolytic properties, anti-pruritic properties, anti-carcinogenic properties. Methods of treatment involving topical application of the preparation are also described.

22 Claims, 13 Drawing Sheets

Day 0

Day 1

Day 2

Day 3

Day 9

Day 21

Day 23

TOPICAL PREPARATIONS

CROSS-REFERENCE TO RELATED APPLICATIONS

This application is a § 371 National Stage Application of International Application No. PCT/EP2021/056268, filed Mar. 11, 2021, and claims priority to United Kingdom Application No. 2003666.1, filed Mar. 13, 2020, each of which is incorporated herein by reference in its entirety.

TECHNICAL FIELD

The invention relates to topical preparations for dermatological application, methods for preparing said preparations and methods of treating dermatological conditions using said preparations.

BACKGROUND

There are hundreds of dermatological ailments that affect humans and animals alike. The symptoms and severity of these dermatological ailments can vary greatly. These ailments may be temporary or permanent in nature. In many cases these dermatological ailments may present in childhood and continue into adulthood. It is common for symptoms not to be continuously present, instead, symptoms flare up at certain times which can be at random or in reaction to environmental factors. When determining the appropriate treatment, skin diseases can be divided into two categories; in situations where the infection is localized to the external skin layers, a topical treatment will suffice. In situations where the infection is widespread and deeper, a systemic treatment will be necessary. In many cases antibiotics are prescribed as the predominant method of treatment. However, the growing overuse of antibiotics is a major concern worldwide. This is due to bacteria developing increased resistance to antibiotics making these dermatological ailments more difficult to treat. Antibiotic resistance has been recognized as a reality since the beginning of the antibiotic era. However, in recent years the occurrence of dangerous, resistant strains of bacteria is becoming more frequent. Overall, antibiotic resistance poses a number of challenges to the healthcare sector including; higher medical costs, prolonged hospital stays and increased mortality.

As an example, the antibiotics Clindamycin and Erythromycin are the topical market leaders for the treatment of acne. The bacteria responsible for acne has shown greater immunity over time to these antibiotics with decreased efficacy to the condition. Similarly, the use of the antibiotic Oxytetracycline for the treatment of digital dermatitis in cattle is showing decreased efficacy for the condition due to increased bacterial resistance. This problem is compounded by antibiotics getting into the food chain where further bacterial resistance occurs within the human population through indirect ingestion.

Current non-steroidal alternatives include crisaborole (Eucrisa™), pimecrolimus (Elidel™) and tacrolimus (Protopic™). Non-steroidal anti-inflammatory drugs (NSAIDs) reduce the production of prostaglandins by inhibiting the enzyme cyclo-oxygenase (COX). Inflammation results during COX enzyme synthesis where prostaglandin is produced. The World Health Organization has issued various warnings on increased resistance of disease like micro-organisms to antibiotics due to overuse. Both Erythromycin and Clindamycin fall into this category.

The traditional treatment of open wounds also poses a number of problems in both animals and humans alike. Depending on the size of the wound, treatment may involve the adaptation of the wound using suture material or staples and/or the application of a dressing and in some extreme cases a skin graft may be necessary. In current methods permanent scarring is an anticipated outcome of wound healing. In humans the presence of scarring on the skin is usually something that renders the individual self-conscious. With larger and more unusually shaped wounds, individuals can present with more permanent low self-esteem. Especially is if the wound is on a commonly exposed area such as face, neck or forearms. In animals the presence of scar tissue is disadvantageous as this can again result in an unattractive appearance. It is common with scarring that an animal's coat will not regrow in a uniform pattern in the area affected. Instead, hair can grow back discolored (i.e., grey) or it will not grow back at all, resulting in bald patches. In areas such as horse breeding/trading where substantial value is placed on the horses overall looks and appearance of health, scarring can result in significant losses in revenue. Furthermore, the presence of scarring in horses can be a source of discomfort to the animal when wearing riding apparatus (bridle, saddle, etc.) as the raised areas of scarring lead to increased friction and perspiration. This can be hugely problematic to horses partaking in equestrian sports and can essentially end their careers.

In both animals and humans alike open wounds when healing can present a number of challenges. In animals, the use of dressings and such is challenging as the animal does not appreciate the sensitivity with which they need to be handled. This can result in the animal, either consciously due to irritation or unconsciously due to lack of awareness, interfering with the dressing which inevitably hinders healing times and can result in infection through the introduction of bacteria into the wound. This is also true for humans particularly in infants and the elderly. Further problems occur where the wound is located on an area that is exposed to constant friction or movement (i.e., on a joint such as the knee or elbow). Persistent opening of the incrustation formed during the healing process, increases healing time and leaves the wound more susceptible to infection. A potentially life-threatening illness such as sepsis is easily contracted through tending to an open wound incorrectly.

In view of the problems associated with orally administered treatments as discussed above coupled with a diminishing antibiotic pipeline, there is a real need for improved and effective topical preparations for dermatological ailments with low toxicity. Furthermore, there is a need for an easy to apply and rapidly effective topical preparation in wound care.

SUMMARY OF THE INVENTION

According to a first aspect of the invention there is provided a topical preparation for dermatological application, the preparation prepared from a mixture comprising:

zinc and/or a salt thereof, salicylic acid and/or a salt thereof and iodine and/or a salt thereof;

in a pharmaceutically acceptable carrier vehicle.

As will be understood, the components used to prepare the topical preparation interact after combining to form a plurality of additional compounds and/or complexes which are believed to contribute to the activity of the preparation and the resulting healing properties.

Zinc may be provided in the preparation as a zinc salt, such as zinc oxide, zinc hydroxide, zinc acetate or zinc sulphate, or any combination thereof. Zinc oxide is preferred. Zinc salts may combine with salicylic acid to form zinc salicylate. When there is a molar excess of zinc oxide or other zinc salt in relation to salicylic acid, not all of the zinc present in the preparation will react to form zinc salicylates. Accordingly, a proportion of zinc oxide or salt may remain in the preparation. If the carrier vehicle comprises an aqueous medium, a proportion of zinc oxide or other zinc salt may be converted to zinc hydroxide ($Zn(OH)_2$).

In one embodiment of the invention the preparation is prepared using zinc salt, preferably as zinc oxide, in a concentration of from 5% to 20% m/m, preferably in a concentration of from 8% m/m to 15% m/m.

Iodine may usefully be provided in the preparation as a solution in ethanol, such as by dissolving iodine crystals in ethanol. Alternatively, iodine may be provided as an iodine salt, such as potassium iodide or sodium iodide, or any combination thereof, with or without molecular iodine. For example, iodine may be provided as a tincture of iodine comprising both molecular iodine and potassium iodide (or sodium iodide), either dissolved in ethanol or a mixture of ethanol and water. Iodine supplied as 2.5% m/m potassium iodide and 2.5% m/m molecular iodine in 95% m/m ethanol may be used, for example.

In one embodiment of the invention the preparation is prepared using iodine or a salt thereof in a concentration of from 0.001% to 10% m/m, preferably in a concentration of from 0.01% m/m to 5% m/m.

As with zinc, iodine may also react with the salicylic acid in the preparation of the invention to form iodo-salicylic acid, which can be mono-, di- and/or tri-iodo salicylic acid. In turn, these various iodo-salicylic acid species may themselves further react with the zinc in the preparation to form zinc iodo-salicylate complexes.

It will be appreciated that there are a number of permutations for the zinc iodo-salicylates that may be formed, depending on whether they are derived from the mono-, di- or tri-iodo salicylic acid form. In particular, the Applicant has identified numerous compounds or complexes that may exist in the preparation as a result of interaction between the zinc, salicylic acid and iodine, some or all of which may contribute to the activity of the preparation according to the invention.

These derivative compounds include: zinc salicylate; 3-iodo salicylic acid; 3-iodo zinc salicylate; 3'-iodo zinc salicylate; 3-iodo, 5'-iodo zinc salicylate; 3-iodo, 3',5'-diiodo zinc salicylate; 3-iodo, 3',4',5'-tri-iodo zinc salicylate; 5-iodo salicylic acid; 5-iodo zinc salicylate; 5'-iodo zinc salicylate; 5-iodo, 3',5'-di-iodo zinc salicylate; 5-iodo, 3',4',5'-tri-iodo zinc salicylate; 3,5-di-iodo salicylic acid; 3,5-di-iodo zinc salicylate; 3',5'-iodo zinc salicylate; 3,5-di-iodo, 3',4',5'-tri-iodo zinc salicylate; 3,4,5-tri-iodo salicylic acid; 3,4,5-tri-iodo zinc salicylate; and 3',4',5'-tri-iodo zinc salicylate.

Further derivative compounds may arise in the preparation when the iodine is supplied in ethanol or a mixture of water and ethanol. For example, ethyl salicylate, di-iodo-ethyl salicylate, zinc ethyl salicylate, 3,5-di-iodo zinc ethyl salicylate.

In one embodiment of the invention the preparation is prepared using salicylic acid or a salt thereof in a concentration of from 1% to 50% m/m, preferably from 2% to 25% m/m, more preferably from 3% to 5% m/m. Typically, higher concentrations of salicylic acid in the preparation are preferred when the preparation is used in the treatment of skin disorders or wounds in animals, as compared to when used in treatment of humans.

Advantageously, in a preferred preparation of the invention, zinc oxide or other zinc salt is used in molar excess with regards to salicylic acid, thereby facilitating generation of a plurality of derivative compounds from the various possibilities described above.

The molar ratio of zinc to salicylic acid may be at least about 1.5:1, preferably at least about 2:1, and more preferably at least about 5:1. The molar ratio of zinc to salicylic acid may be at most 25:1, preferably at most 20:1, and more preferably at most 10:1. In an embodiment, the molar ratio of zinc to salicylic acid is about 8.5:1, or about 5:1.

Advantageously, salicylic acid is used in molar excess with respect to iodine content. Preferably the molar ratio of salicylic acid to iodine (as molecular iodine, or molecular iodine and potassium/sodium iodide combined if supplied to the preparation as a tincture) is at least about 1.5:1, preferably at least about 5:1, and more preferably at least about 10:1. The molar ratio of salicylic acid to iodine may be at most 25:1, preferably at most 20:1, and more preferably at most 15:1. In an embodiment, the molar ratio of salicylic acid to iodine is about 10:1.

The pharmaceutically acceptable carrier vehicle may be a cream, ointment, lotion, gel or any other suitable pharmaceutically acceptable base for dermatological application. For example, the carrier vehicle may be selected from any one or more of emulsifying ointment, aqueous cream, castor oil cream, hydrogel, alginate hydrogel, liquid paraffin, white soft paraffin, 50/50 liquid paraffin/white soft paraffin or any combinations thereof.

Aqueous cream is especially preferred for use as, or a component of, the carrier vehicle. Such an aqueous cream may comprise a blend of emulsifying ointment, white soft paraffin and liquid paraffin, preferably in amounts of 30% w/w, 15% w/w and 6% w/w respectively, with a balance of purified water. The emulsifying ointment of the aqueous cream preferably comprises emulsifying wax containing cetostearyl alcohol (such as in an amount of about 8% m/m) and sodium laurylsulfate (such as in an amount of about 1% m/m), with liquid paraffin, white soft paraffin and purified water. Phenoxyethanol may also be included in the aqueous cream as a preservative, such as in an amount of about 1% w/w. Other excipients may include methyl paraben, ethyl paraben and propyl paraben.

Advantageously, a carrier vehicle comprising a combination of aqueous cream and castor oil may be used. For example, the preparation of the invention comprises the zinc, salicylic acid and iodine components and their derivatives, with the carrier vehicle comprising castor oil in an amount of from 5% to 40% m/m, and aqueous cream ad. 100% m/m.

The aqueous cream may comprise various emollients, emulsifiers, stabilizers and combinations thereof. Stearate emulsifiers are preferred, especially sugar-based stearates, for example, glyceryl stearate, sucrose stearate and combinations thereof;

these have been shown to provide excellent stability and shelf-life in the formulations according to the invention, as well as enhancing the antimicrobial properties thereof. The quantity of emulsifier(s) used is adjusted according to the desired viscosity of the preparation.

Blends of sucrose stearates may be used, for example, a blend of sucrose stearate HLB 11 and sucrose stearate HLB 15. In one application of the invention, the preparation may comprise from 1 to 5% m/m of sucrose stearate HLB 11 and from 1 to 10% m/m of sucrose stearate HLB 15.

In one embodiment, the topical preparation of the invention is prepared from a mixture of 2% m/m salicylic acid, 6% m/m tincture of iodine (0.01% m/m iodine), 10% m/m zinc oxide, 6% m/m castor oil and 76% m/m aqueous cream. The aqueous cream may comprise emulsifying wax, cetostearyl alcohol, sodium laurylsulfate, purified water and white soft paraffin. Such a preparation approximates to a molar ratio of salicylic acid:KI:$I_2$.:zinc oxide of 1:0.06:0.04:8.5.

In one embodiment of the invention the preparation is prepared using zinc, salicylic acid and iodine, including salts thereof, in the aforementioned molar amounts with the balance being a pharmaceutically acceptable carrier vehicle selected from any one or more of: emulsifying ointment, aqueous cream, castor oil cream, hydrogel, alginate hydrogel, liquid paraffin, white soft paraffin, 50/50 liquid paraffin/white soft paraffin or combinations thereof. Accordingly, in one embodiment the preparation may be in the form of a cream, ointment, paste, lotion, gel, wash, solution, powder or hydrogel.

In one embodiment of the invention, the preparation is prepared using 3% m/m salicylic acid, 3% m/m tincture of iodine (0.01% m/m iodine) and 6% m/m zinc oxide, with the balance being 20% m/m castor oil and 68% m/m aqueous cream. The aqueous cream may comprise glyceryl stearate, cetyl alcohol, xanthan gum, sucrose stearate and purified water.

According to another aspect, the topical preparation according to the invention is for use in the treatment of dermatological ailments. The topical preparation may be used in the treatment of humans or in veterinary treatment, especially of mammals, or both. In particular, the preparation is for use as an anti-inflammatory treatment, or a keratolytic treatment, or an anti-pruritic treatment, or an anti-carcinogenic treatment.

In clinical applications, the topical preparation of the invention has been observed to alleviate the following conditions in humans: wound healing, including but not limited to wounds resulting from trauma or injury, poor circulation or pressure, such as skin ulcers, especially diabetic skin ulcers; rosacea; herpes infections, including cold sores; eczema; psoriasis; acne; impetigo; infections of the dermis (bacterial, fungal, viral); inflammatory conditions of the dermis; and pruritis.

In animal applications, the preparation of the invention has been seen to be particularly effective in relation to wound healing, infections of the dermis, inflammatory conditions of the dermis, and in digital dermatitis.

In one aspect, the preparation is effective for alleviating the symptoms of summer seasonal recurrent dermatitis (SSRD), a disease of the immune system that affects all breeds and types of horses, ponies and donkeys and results from hypersensitivity to biting insects. SSRD is often referred to as "sweet itch" and is the most common allergic skin condition in horses, often progressing from intense itching to hair loss, skin thickening and ultimately causing behavioural issues.

In another aspect, the preparation may also be used on companion animals, for example, to treat atopic dermatitis. Feline and canine atopic dermatitis is an increasingly prevalent condition and has traditionally been treated with glucocorticoids, ciclosprorin and/or antihistamines. Accordingly, treatment based upon the topical preparation according to the present invention is advantageous as it is of low toxicity and can be readily applied to affected areas.

As well as alleviating symptoms of dermal complaints and infections, and promoting wound healing, the preparations according to the invention may be used topically as a prophylactic treatment. For example, the preparation may be used as an anti-parasitic preparation, including as an insect repellant, especially against biting insects, and thereby reducing the opportunity for parasitic infections to establish.

The preparation of the invention has also been seen to be effective in supporting hair regrowth at wound sites. Thus, the preparation may promote both re-epithelialization and development of new hair follicles.

The preparation of the invention when applied topically is effective in antiseptic and healing processes and may also play an important part in the whole immune response process in the body.

As hereinbefore described, the topical preparation of the invention is prepared from a mixture of zinc, zinc oxide and/or other zinc salt, salicylic acid and/or a salt thereof, and iodine and/or a salt thereof, which react in the mixture to produce derivatives of zinc, salicylic acid and iodine.

According to another aspect of the invention, there is also provided a method of preparing a topical skin treatment preparation comprising:— preparing a mixture of salicylic acid and/or a salt thereof with zinc and/or a zinc salt;

adding a pharmaceutically acceptable carrier vehicle to the salicylic acid/zinc mixture;

adding iodine and/or an iodine salt to the carrier vehicle/salicylic acid/zinc mixture;

optionally adding a further quantity of pharmaceutically acceptable carrier vehicle to the carrier vehicle/salicylic acid/zinc/iodine mixture;

and agitating the resulting mixture to provide a homogenized preparation.

Preferably the salicylic acid component is provided in powder form, and the zinc component is also provided in powder form. The powders are preferably milled together after combining to produce a fine consistency.

The salicylic acid/zinc mixture is preferably mixed with the pharmaceutically acceptable carrier vehicle to form a paste. Advantageously, the carrier vehicle comprises castor oil. The iodine is preferably added as a solution, such as iodine dissolved in ethanol, and mixed with the paste to form a light paste. On mixing the iodine with the paste, a change in colour of the resulting mixture may be observed, indicating that iodine is combining with the salicylic acid and zinc, and the resultant salicylic acid/zinc derivatives, to form various iodo-salicylic acid species and zinc iodo-salicylate complexes.

Further base carrier, which may the same or different to that initially added to form the paste, may then be added to achieve a desired consistency for topical application.

The resulting combination is then agitated, for example by means of a blender, to produce a homogenized mixture. Agitation may be performed for thirty minutes or longer, preferably for at least one hour, to ensure homogenization and reaction between the salicylic acid, zinc and iodine to form iodo-salicylic acid species and zinc iodo-salicylate complexes.

Agitation of the mixture may be performed at raised temperature, for example at from 50° C. to 100° C., preferably at from 70° C. to 90° C., and most preferably about 80° C. Raising the temperature during agitation may contribute to the formation of the aforementioned species and complexes.

Further, agitation at raised temperature may be performed under vacuum to aid in reduction of moisture content in the preparation.

In an alternative method of preparing a topical skin treatment preparation according to the invention, salicylic acid and/or a derivative thereof is mixed with a zinc salt;

preferably the salicylic acid and zinc salt are both in powder form and the mixture is milled to a fine consistency;

iodine is added to the milled mixture, preferably as iodine in ethanol solution, and the resulting combination is agitated for a period, such as from 30 mins to 2 hours, to allow for homogenization;

the resulting homogenized salicylic acid/zinc/iodine mixture is dried at elevated temperature, such as at from 50° C. to 100° C., preferably at from 70° C. to 90° C., and most preferably about 80° C., optionally under agitation, to obtain a dry, base powder.

The drying step may take place under partial or full vacuum to accelerate removal of moisture and/or solvent introduced with the iodine. Use of a microwave dryer is preferred.

The dry base powder may then be combined with a pharmaceutically acceptable carrier vehicle to produce a preparation for topical application.

In yet another method of preparing a topical skin treatment preparation according to the invention, the pharmaceutically acceptable carrier vehicle may be prepared, and iodine added the carrier vehicle prior to addition of zinc salt and salicylic acid. The carrier vehicle is preferably heated to above ambient temperature prior to addition of iodine.

In a preferred method, iodine is added to water that has been pre-heated, for example to between about 40 to 50° C., and the resulting aqueous iodine mixture is added to castor oil, also preheated to about 50 to 60° C. The castor oil may be pre-mixed with one or more stabilizers and/or emulsifiers prior to combining with the aqueous iodine mixture, preferably the pre-mixing is performed after the temperature of the castor oil has been raised. Further emulsifiers may be added following addition of the zinc salt and salicylic acid to the combined castor oil/aqueous iodine mixture. The entire preparation is thoroughly mixed, preferably in a blender or the like, for a period to ensure homogeneity.

From another aspect, the present invention further resides in a method of treating a dermatological condition in a human or animal, comprising topical administration of a preparation as hereinbefore described in any of the aforementioned aspects. For example, the invention may reside, but is not limited to, methods of treating skin disorders such as psoriasis, rosacea, SSRD, etc. as well as treating skin wounds, such as those resulting from trauma or from other conditions that result in laceration of the skin.

BRIEF DESCRIPTION OF THE DRAWINGS

The invention will now be further described and illustrated, by way of example only, with reference to the accompanying drawings in which.

DETAILED DESCRIPTION

Figures 1A, 1B:
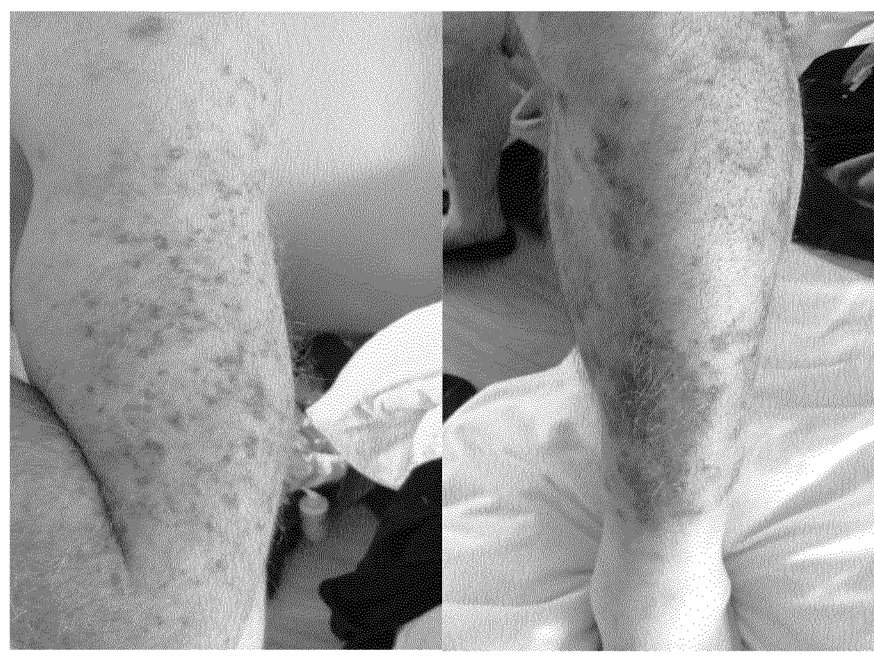
FIGS. 1(*a*) to 1(*d*) illustrate the results of using a preparation in accordance with the invention in the treatment of psoriasis on human arms and legs.

As hereinbefore described, the present invention provides a range of novel and improved topical preparations with low toxicity for use in treating dermatological ailments. The preparations may be used for both human and veterinary use. The present invention further provides a method of treating dermatological conditions in humans and animals through topical administration of said preparations.

The novel compositions of the topical preparations play an important part in antiseptic and healing processes and also play a role in the whole immune response process in the body.

To assist in the understanding of the invention, a number of definitions are hereinbelow set forth.

As used herein, the term “comprising” means any of the recited elements are necessarily included and other elements may optionally be included as well. “Consisting essentially of” means any recited elements are necessarily included, elements that would materially affect the basic and novel characteristics of the listed elements are excluded, and other elements may optionally be included. “Consisting of” means that all elements other than those listed are excluded. Embodiments defined by each of these terms are within the scope of this invention.

“Anti-inflammatory properties”— the ability to reduce inflammation or swelling by counteracting the effect of the cyclooxygenase (COX) enzyme which in turn affects the production of prostaglandins which are through vasodilation involved in inflammation. Prostaglandin-endoperoxide synthase (PTGS) (more commonly known as Cyclooxygenase (COX)) is an enzyme that is associated with the formation of prostaglandins from arachidonic acid. These prostaglandins are integral in a range of both physiological and pathophysiological processes including inflammation, reproduction, nociception. Two COX isoforms have been identified; COX-1 which is constitutively expressed in most tissues and COX-2 which participates in inflammation.

“Keratolytic properties”—the ability to break down the outer layers of the skin to decrease the thickness of the psoriatic plaques.

“Anti-pruritic properties”—the ability to inhibit itching, local anesthetic action is achieved in topical agents by stabilizing the neuronal membrane and preventing the initiation and transmission of nerve impulses. (Itching may also be controlled by oral agents by blocking the effects of the endogenously released histamine.)

“Anti-carcinogenic properties”—the ability to counteract the effects of a carcinogen or inhibit the development of cancer.

“Acne vulgaris” (commonly referred to as acne) is an inflammatory skin disorder affecting the pilosebaceous unit. It can present with both inflammatory and non-inflammatory lesions. These lesions chiefly appear on the face but can also appear on the upper arms, trunk and back. Acne can be identified by open or closed comedones, and/or by erythematous papules and pustules on the face, as well as erythema on the surrounding skin. It manifests when hair follicles become clogged with oils and dead skin causing inflammation. Acne can result from a range of factors including genetics, hormonal function and bacterial growth.

"Acne Rosacea" (commonly referred to as Rosacea) is a chronic inflammatory skin condition characterized by redness, flushing and visible blood vessels. Often these symptoms can be additionally accompanied by small, red pus-filled bumps that are similar to acne and/or irritated, swollen and reddened eyelids. These symptoms predominantly affect the face. There are four subtypes of rosacea which may overlap.

While no single root cause of rosacea is known, factors including alcohol, spicy food and alcohol have been known to exacerbate the condition.

"Atopic Dermatitis" (commonly referred to as Eczema) is an inflammatory skin condition that can be characterized by dry, pruritic skin with a chronic relapsing course; it affects individuals of all ages, although diagnosis usually occurs at the infant stage typically before five years of age, as well as being a common condition in companion animals. It can accompany other atopic diseases and it can present in acute or chronic form. It most commonly affects the creases in the joints at the elbows and knees along with the wrists and neck.

"Psoriasis" is a chronic skin condition that speeds up the life cycle of skin cells. A build-up of cells occurs on the surface of the skin. These cells appear as thick, white, silvery or red patches of skin (known as plaques). There are five subtypes of psoriasis characterized by different plaques. These plaques most often appear on the knees, elbows scalp, hands, feet and lower back. It is not known what causes psoriasis. It is thought that T-cells travelling through the body to detect and combat invading germs begin to attach healthy skin cells by mistake causing the deepest skin layer to produce new skin cells more rapidly. However, the exact reasoning for the T-cell malfunction is not known. Psoriasis can be treated through the use of topical treatments, phototherapy and tablet and/or injectable systemic treatment.

"Cellulitis" is a bacterial infection that affects the dermis and subcutaneous tissues. The skin appears swollen and red with the individual experiencing pain and heat in the region affected. It most commonly appears on the legs but can also occur in other areas including the face, arms and neck. Cellulitis occurs when certain types of bacteria (most commonly *streptococcus* and *staphylococcus*) enter the skin through a cut or lesion. Therefore, individuals presenting with eczema or psoriasis can have a higher risk of developing cellulitis.

"Herpes simplex virus" (commonly referred to as Herpes) is a viral infection that can affect different areas of the dermis but primarily affects the external genitalia, anal region and mucosal surfaces. It is a long-term condition, and an individual does not have to present with symptoms to be infected. There are two types of herpes simplex virus: HSV-1 which typically affects the oral region and HSV-2 which typically affects the genitalia. Symptoms usually include blisters and ulceration in the infected region. Pain and itching commonly accompany such blisters. Other symptoms can include general malaise, high temperature and tender/enlarged lymph nodes. Although there is no cure for herpes, it can be treated using antiviral medications such as acyclovir. Such medications help to prevent the virus from multiplying and reduce the severity of the symptoms but cannot eradicate the virus entirely.

"Impetigo" is a highly contagious infection of the dermis. Symptoms typically include the appearance of a rash comprising blisters or sores that ooze before drying up and forming a crust, the blisters appear on the trunk, legs and arms. In addition to these blisters the individual will typically experience fever and swollen glands. The infection can be caused by either *Staphylococcus aureus* or *Streptococcus pyogenes* entering the skin. This can occur without an established site of entry and is known as primary impetigo. Alternatively, the bacteria can enter through a disruption to the skin that has been previously established known as secondary impetigo. The disruption may result from a skin condition, wound or bite. Impetigo is usually treated with antibiotics; either in topical or oral form. In very mild instances, keeping the skin clean may be sufficient to treat the infection.

"Digital dermatitis" is an infectious condition primarily affecting the skin on the heel of bovines, although it can occur in other areas. Treponeme bacteria are the primary pathogens responsible for the diseases. It is a highly contagious and can cause pain and discomfort and ultimately results in lameness. Bovines infected with the disease present with lesions. There are five different lesion categories associated with each stage of the disease. Digital dermatitis arises is unsanitary, damp conditions. Typical treatment involves topical application of Oxytetracycline.

"Wound healing" as used herein refers to a sequence of molecular and cellular events in which tissue repair and regeneration take place to restore damaged tissue after the onset of a lesion.

"Epithelialization" is used as a defining parameter of successful wound closure in wound healing. It involves both the cellular and molecular processes involved in the initiation, maintenance and completion of epithelization.

The topical preparations of the present invention have a broad spectrum of germicidal activity against bacterial, fungal and viral infections as well as fast wound healing properties, anti-inflammatory properties and anti-pruritic properties.

The preparations are prepared from a mixture of three active base ingredients, salicylic acid, iodine and zinc in different concentrations and added to different forms of topical vehicles such as creams, ointments, powders, pastes, lotions, suspensions, solutions, washes, hydrogels and mixtures thereof.

The basic preparations comprising the active ingredients salicylic acid, iodine and zinc may be used as a base for the addition of other ingredients including corticosteroids and coal tar for the treatment of other dermatological ailments. Examples of such dermatological ailments include eczema, psoriasis and various forms of skin disease.

The active ingredients are combined within a pharmaceutically acceptable carrier base, such as those hereinbefore described.

Salicylic acid is a lipophilic mono-hydroxybenzoic acid that functions as a plant hormone and is used as a key ingredient in topical preparations to treat skin related conditions such as acne and psoriasis among others. Used topically, salicylic acid works as a keratolytic, comedolytic and bacteriostatic agent. It works by lowering the pH of the skin, resulting in increased hydration and swelling of corneocytes. Desquamation is also facilitated through the solubilizing of the intercellular cement substance. Salicylic acid has anti-inflammatory, anti-pyretic and anti-pruritic properties. Salicylic acid has been shown to suppress proteins responsible for cellular damage caused by inflammation. Salicylic acid promotes apoptosis, induces exfoliation and causes shedding of the outer layer of the skin. The concentration of salicylic acid used in the preparations of the present invention is in the range of 1% to 50 m/m %. When using the preparation in relation to animals the concentration of salicylic acid may exceed 50 m/m %.

Zinc is a chemical element belonging to the transition metal group of the periodic table. Zinc is of exceptional biological and public health importance. It is an essential trace element for humans and animals and is to be found in over 300 enzymes. Between 2 to 4 grams of zinc are distributed throughout the body with up to 20% of this found in the skin. Zinc has roles in the metabolism of RNA and DNA signal transductions and gene expressions. Zinc plays an important role in wound repair via regulation of DNA and RNA polymerases thymidine. Zinc has been used for the treatment of various dermatological disorders including acne vulgaris, eczema, psoriasis, warts, rosacea, and ulcers, it has antibacterial and antifungal activity and is used in wound treatment. All forms of zinc derivatives and salts may be used in the preparations of the present invention including but not limited to zinc oxide, zinc acetate and zinc sulphate.

Zinc complexes of simple phenolic compounds are more potent than zinc ions alone as the binding of metal ion complexes occurs at specific sites on the DNA. This induces apoptosis of cells. The process is associated with the cell cycle and is regulated by cyclin-dependent kinase (CDKs) and caspases. Cell cycle progression is regulated by the synthesis of CDKs at different phases. Cyclins are a group of regulated proteins and are among the most important core cell cycle regulators. In order to drive the cell cycle forward a cyclin must activate or inactivate many target proteins inside of the cell. Cyclins drive the events of the cell cycle by partnering with a family of enzymes called the cyclin-dependent kinases (CDK's). A lone CDK is inactive but the binding of a cyclin activates it making it a functional enzyme and allowing it to modify target proteins.

Zinc oxide in particular is a known safe and effective active sunscreen agent, with the ability to block the sun's UVA and UVB radiation from being absorbed into the dermis. The concentration range for zinc oxide used in the preparations of the present invention is preferably from 5% to 20%, more preferably from 7% to 15% and most preferably from 10% to 14%.

Zinc salicylate is a very powerful antiseptic and astringent. It is formed when zinc oxide complexes with salicylic acid in the presence of water. The ratio of the complex affects the aqueous solubility, with the 2:1 complex of salicylic acid to zinc having higher aqueous solubility than the 1:1 complex.

Iodine is a chemical element of the halogen group in the periodic table. Iodine is used as an antiseptic and is effective against bacteria, fungi, viruses and yeasts even at small concentrations. Bacteria do not develop resistance to iodine, it is effective at reducing wound size and bacterial count. The preparations of the present invention may use iodine in any form and concentration including tincture of iodine, povidone and a solution of iodine in ethanol. The concentration of iodine used in the preparations of the present invention may range from 0.001% to 10% m/m. The concentration of the iodine used will depend on the concentration of other ingredients and the condition to be treated. Some iodine will react with zinc and salicylic acid thus reducing the availability of free iodine.

Zinc iodide is used as an antiseptic and astringent for topical use. Zinc iodide is formed through the direct reaction of the zinc, typically provided as zinc oxide in powder form, with iodine in ethanol. The reaction that occurs is an exothermic redox, with the resulting product being zinc iodide once the solvent has been evaporated off. It is believed that the formation of zinc iodide and other zinc-iodo species can be observed through colour change. In particular, the reaction is known to proceed as the brown colour of the iodine solution disappears. Without wishing to be bound by theory, it is thought that the interaction between the iodine and zinc is minimal at first. However, the zinc complexes with salicylic acid in the presence of water to form either a 2:1 or 1:1 salicylic acid to zinc molar ratio complex. Once the zinc has been solubilized as the zinc salicylate then there is potential for the zinc cation to react with the iodide, resulting in zinc iodide.

Thus, it will be understood that the preparation according to the invention comprises a host of derivatives that result from the combination of salicylic acid, zinc and iodine which are believed to contribute to surprising and unexpected activity in the treatment of dermatological ailments.

Structures of the various derivatives and complexes that may arise in the preparation according to the invention are provided in Tables A to D below:

TABLE A

| Structures of 5-Iodo Salicylic acid and its complexation permutations with zinc |
| --- |
| 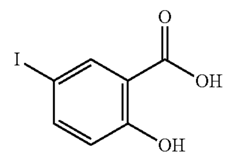 [SMILES: O=C(O)c1cc(I)ccc1O] |
| 5-Iodo Salicylic acid |
| 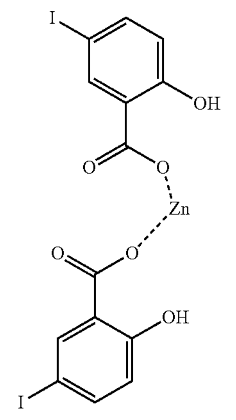 |
| 5-Iodo Zinc salicylate |
| 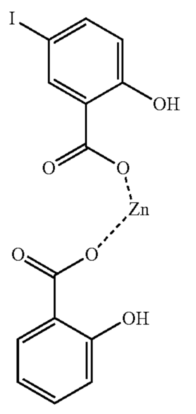 |

TABLE A-continued

| Structures of 5-Iodo Salicylic acid and its complexation permutations with zinc |
| --- |
| 5'-Iodo Zinc salicylate |
| 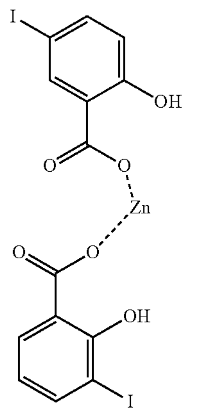 |
| 5-Iodo, 3'-Iodo Zinc salicylate |
| 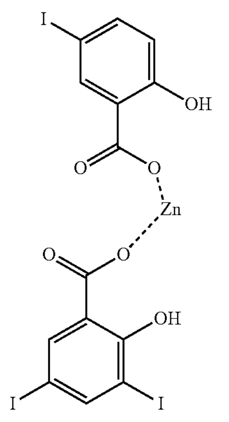 |
| 5-Iodo, 3',5'-Di-iodo Zinc salicylate |
| 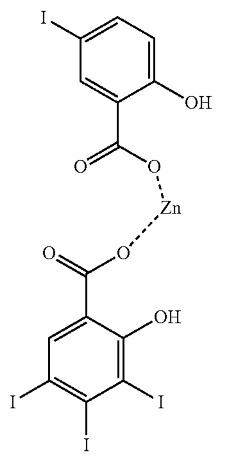 |
| 5-Iodo, 3',4',5'-Tri-iodo Zinc salicylate |

TABLE B

| Structures of 3,5-Di-iodo Salicylic acid and its complexation permutations with zinc |
| --- |
| 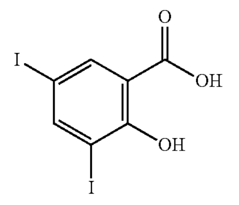 [SMILES: O=C(O)c1cc(I)cc(I)c1O] |
| 3,5-Di-iodosalicylic acid |
| 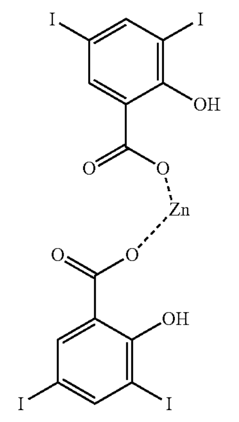 |
| 3,5-Di-iodo Zinc salicylate |
| 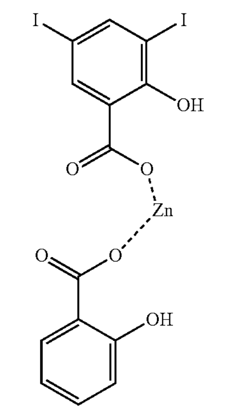 |
| 3',5'-Iodo Zinc salicylate |
| 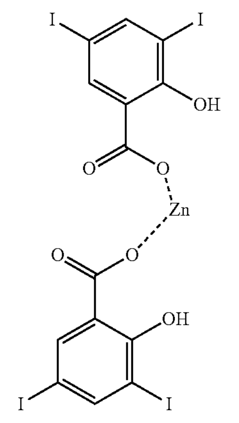 |
| 3,5-Di-iodo, 3'-Iodo Zinc salicylate |

TABLE B-continued

Structures of 3,5-Di-iodo Salicylic acid and its complexation permutations with zinc

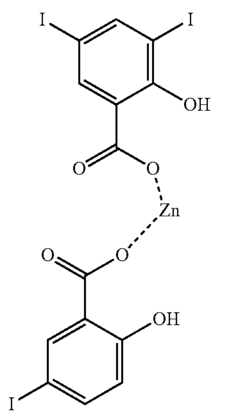

3,5-Di-iodo, 5'-Di-iodo Zinc salicylate

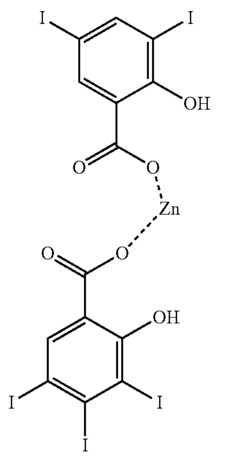

3,5-Di-iodo, 3',4',5'-Tri-iodo Zinc salicylate

TABLE C

Structures of 3,4.5-Tri-iodo Salicylic acid and its complexation permutations with zinc

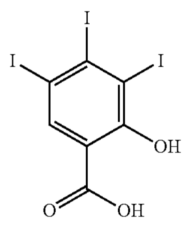 [SMILES: O=C(O)c1cc(I)c(I)c(I)c1O]

3,4,5-Tri-iodosalicylic acid

TABLE C-continued

Structures of 3,4.5-Tri-iodo Salicylic acid and its complexation permutations with zinc

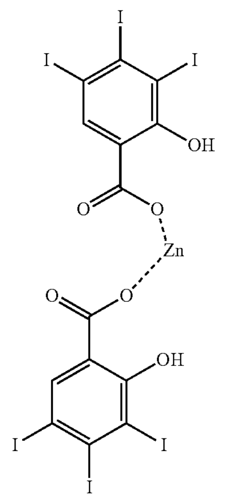

3,4,5-Tri-iodo Zinc salicylate

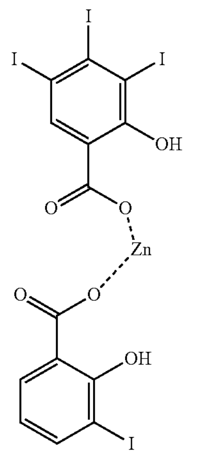

3,4,5-Tri-iodo, 3'-Iodo Zinc salicylate

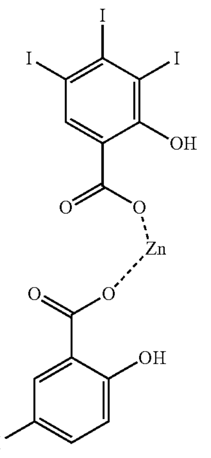

3,4,5-Tri-iodo, 5'-Iodo Zinc salicylate

TABLE C-continued

| Structures of 3,4,5-Tri-iodo Salicylic acid and its complexation permutations with zinc |
|---|
| 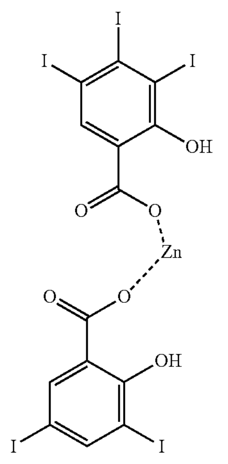 |
| 3,4,5-Tri-iodo, 3',5'-Di-iodo Zinc salicylate |
| 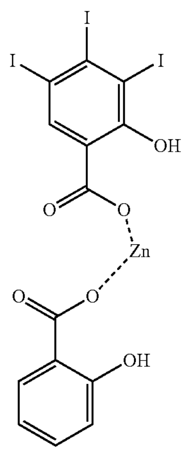 |
| 3',4',5'-Tri-iodo Zinc salicylate |

TABLE D

| Structures of ethyl salicylate and its complexation permutations with iodine and zinc |
|---|
| 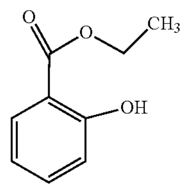 |
| Ethyl Salicylate |
| 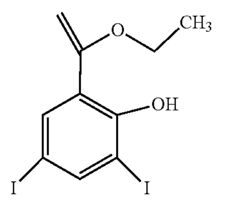 |

TABLE D-continued

| Structures of ethyl salicylate and its complexation permutations with iodine and zinc |
|---|
| Di-iodo Ethyl Salicylate |
| 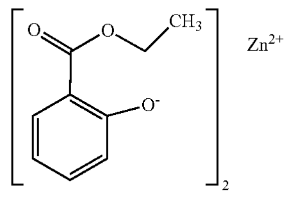 |
| Zinc Ethyl Salicylate |
| 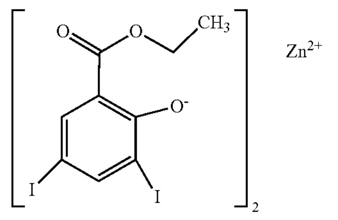 |
| 3,5-Di-iodo Zinc Ethyl Salicylate |

As will be understood, the specific concentration of active ingredients and the carrier vehicle used may be optimized depending on the specific dermatological condition being treated.

The preparations of the present invention have shown 100% germicidal activity as a result of the combined activity of iodine, salicylic acid and zinc. The preparation formed from the mixture of the three components has been shown to enhance the repair of the dermis substantially, and all microbes including bacteria, viruses and fungi including spores are eliminated. Moreover, microbes do not develop resistance to the preparations.

The preparations of the present invention accelerate the healing process of all wounds; the preparations have anti-inflammatory properties; the preparations are anti-pruritic; the preparations are anti-carcinogenic; and the preparations have keratolytic properties and inhibit dermal auto immune disorders.

The preparations of the invention may also act as a sunscreen to prevent further damage to the wound or skin while exposed to sunlight.

The preparations of the invention inhibit enzymes produced by some microbes that cause scarring of the skin. Without wishing to be bound by theory, the enzyme lysyl oxidase (LOX) has been shown to be responsible for scar formation through crosslinking in the collagen involved in the wound healing. LOX catalyzes the formation of aldehydes from lysine in collagen and elastin precursors. Due to the reactivity of the aldehydes, spontaneous cross-linking occurs. Evidence suggests that LOX inhibition is capable of altering the collagen architecture and permitting restoration of the normal appearance and pattern of the skin.

Without wishing to be bound by theory, di-iodo zinc salicylate appears to function in a similar manner to thyroxine hormones. Thyroxine hormones work intracellularly to increase base metabolic rate. In relation to dermatological application, it is postulated that due to the bio similarity of di-iodo zinc salicylate to thyroxine, healing and re-epithelialization of the affected site improves through increased metabolism and increased blood supply.

From another aspect, the invention resides in a thyroxine hormone mimetic comprising a topical preparation as hereinbefore described in accordance with the first aspect of the invention.

Many known pharmaceutical bases may be used as the carrier vehicles for the salicylic acid, zinc and iodine. Paraffin gel, emulsifying ointment, purified water or castor oil soap are among those bases that are suitable. The proportions in which the same ingredients are mixed can determine the structural forms of the resulting preparation. The tactile properties of topical preparations are important in determining product choice by consumers or for the adherence to treatment. For cosmetic preparations, odour may also be an important factor in the attractiveness of a product in the treatment of for example acne. The pH of the preparations will preferably be maintained at around 5.5 to 6 which is the pH of human skin.

There now follows some examples of topical preparations in accordance with the invention and their use for treating dermatological ailments. Unless stated otherwise, amounts in percentages are expressed as m/m.

Example 1

A pharmaceutical composition according to the invention is prepared for topical application to the epidermis/dermis as follows:

(i) Preparation of a Base Powder

Step 1:200 grams of salicylic acid powder is mixed with 100 grams of zinc oxide powder until homogenization is achieved;

Step 2: The resultant powder is milled until a very fine consistency is achieved;

Step 3: A mixture of iodine in ethanol (5% solution) is added and the resulting composition is agitated for one hour;

Step 4: The resulting composition is placed in a microwave dryer under slight vacuum to recover the alcohol and dried at 80° C. while continuing to agitate until a dry fine powder is achieved.

Heating the mixture at 80° C. accelerates the reactions between the ingredients to achieve new derivative compounds such as di-iodo zinc salicylate.

The resultant base powder may contain any one or more of salicylic acid, zinc oxide, zinc iodide, zinc salicylate and di-iodo zinc salicylate.

The concentrations of the constituents in the base powder may be varied according to intended therapeutic use. Use of zinc oxide and salicylic acid in powder form allows for concentrations to be readily adjusted.

(ii) Preparation of Topical Formulation

The base powder is then combined with a pharmaceutically acceptable carrier vehicle, such as a combination of castor oil and aqueous cream, to produce a preparation ready for topical application, as exemplified below.

Example 2: Preparation of Topical Paste, Etc.

The appropriate quantities of salicylic acid powder and zinc salt are milled together until a fine powder is obtained. The powder is triturated with a portion of the carrier vehicle until a smooth paste results. The carrier vehicle may be castor oil, however any suitable carrier vehicle may be used. These include white soft paraffin, liquid paraffin, emulsifying ointment, aqueous cream, castor oil cream BP, and various creams, ointments, lotions, shampoos, or gels. The appropriate quantity of iodine is added with further mixing until the desired consistency is achieved. The iodine may be in the form of iodine in ethanol, tincture of iodine or povidone or any other suitable iodine salt including zinc iodide. The frictional heat generated through the milling and mixing process aids the formation of associated compounds such as zinc iodide and zinc salicylates. The balance of the carrier vehicle is then added to the smooth paste while mixing and the final product is mixed until homogenized.

The following examples show the range of products using different concentrations and salts of the active ingredients, and various vehicles:

A Topical Cream

| Rx | |
|---|---|
| Zinc Oxide | 100 g |
| Salicylic Acid | 20 g |
| Tincture of Iodine | 100 g |
| Emollient | 780 g |

A Topical Ointment

| Rx | |
|---|---|
| Zinc Oxide | 100 g |
| Salicylic Acid | 20 g |
| Tincture of Iodine | 100 g |
| Paraffin Gel | 780 g |

A Topical Paste

| Rx | |
|---|---|
| Zinc Oxide | 100 g |
| Salicylic Acid | 10 g |
| Tincture of Iodine | 50 g |
| Emulsifying Ointment | 240 g |

A Topical Lotion

| Rx | |
|---|---|
| Zinc Oxide | 100 g |
| Salicylic Acid | 20 g |
| Tincture of Iodine | 100 g |
| Sodium Alginate | 20 g |
| Purified Water | 760 g |

A Topical Wash

| Rx | |
|---|---|
| Zinc Oxide | 100 g |
| Salicylic Acid | 20 g |
| Tincture of Iodine | 100 g |
| Castor Oil Soap BP | 780 g |

A Topical Cream

| Rx | |
|---|---|
| Zinc Sulphate | 100 g |
| Salicylic Acid | 20 g |

-continued

| Rx | |
|---|---|
| Povidone-iodine 8% | 100 g |
| Emollient | 780 g |

The preparations according to the present invention may include additional pharmaceutically acceptable carriers, adjuvants, and/or biologically active substances.

Example 3: Preparation for Topical Application

A preparation for topical application was prepared comprising:

5% m/m Zinc Oxide

3% m/m Salicylic Acid 0.5% m/m Iodine

4% m/m Ethanol

Ad to 100% Carrier (oil and water emulsion)

The above preparation was analyzed for bacteria regeneration using preservative efficacy testing (PET) method. The strains of bacteria tested for were; *Pseudomonas aeruginosa, Escherichia coli, Staphylococcus aureus, Aspergillus brasiliensis, Candida albicans*. The product was sampled at day 0, day 14 and day 28. As shown in Table D below, the tests run with a higher concentration of product show a lower percentage recovery overall. In the case of *Aspergillus brasilensis* 0% recovery was observed with a 1:10 product dilution as opposed to 100% recovery with a 1:100 product dilution.

TABLE D

| Reference Strains Bacteria | Product Dilution | Control (cfu/ml) | Sample (cfu/ml) | % Recovery | Pass/Fail |
|---|---|---|---|---|---|
| *Pseudomonas* | 1:10 | 22 | 1 | *5 | Fail |
| *aeruginosa* | 1:100 | | 9 | *41 | Fail |
| *E. coli* | 1:10 | 63 | 1 | *2 | Fail |
| | 1:100 | | 29 | *46 | Fail |
| *Staphylococcus* | 1:10 | 70 | 21 | *30 | Fail |
| *aureus* | 1:100 | | 78 | 111 | Pass |
| *Aspergillus* | 1:10 | 14 | <1 | *0 | Fail |
| *brasiliensis* | 1:100 | | 14 | 100 | Pass |
| *Candida* | 1:10 | 41 | 2 | *5 | Fail |
| *albicans* | 1:100 | | 25 | 85 | Pass |
| Sterility Inactivation Broth & Product No Spike | | <1 | <1 | <1 | Pass |

Example 4: Preparation for Topical Application

A preparation according to the invention was prepared from the following ingredients, the concentrations being the initial concentrations as added:

TABLE E

| Ingredient | | Preparation concentration | Molar ratio in |
|---|---|---|---|
| | Composition | (% m/m) | preparation |
| Salicylic Acid | — | 2 | 0.118 |
| Tincture of Iodine | — | 6 | — |
| | KI | 2.5 | 0.007 |
| | $I_2$ | 2.5 | 0.005 |
| | EtOH | 95 | 0.132 |
| Zinc Oxide | — | 10 | 1 |
| Castor oil | — | 6 | 0.052 |
| Aqueous cream | | 76 | Not determined |
| | Emulsifying Wax | — | — |
| | Cetostearyl alcohol | — | — |
| | Sodium laurilsulfate | — | — |
| | Purified water | — | — |
| | White Soft Paraffin | — | — |

Samples were prepared in accordance with the above preparation, but in which the primary components, namely salicylic acid, zinc and iodine, were included or excluded in different combinations as follows:

Sample 1: Salicylic acid+ZnO

Sample 2: Salicylic acid+(tincture of iodine)

Sample 3: ZnO+(tincture of iodine)

Sample 4: Salicylic acid+ZnO+(tincture of iodine)

Testing of the samples was conducted using nuclear magnetic resonance (NMR), scanning electron microscope (SEM/EDX) and infra-red spectroscopy (FT-IR), together with a simple visual inspection. These tests indicated that there was some interaction between the salicylic acid and the iodine, but that there was a strong interaction between the salicylic acid and zinc. Moreover, from the visual inspection it was observed that Samples 1, 2 and 4 all resulted in a colourless solution, indicating that iodine was consumed. Overall, the results suggested that there is complexation between elemental zinc and salicylic acid to form zinc salicylates, and that iodine does not react strongly with zinc, but reacts with the salicylic acid to form iodo-salicylic acid (which can be mono-, di- and/or tri-iodo salicylic acid) and these iodo-salicylic acid species react with the zinc to form zinc iodo-salicylate complexes.

Example 5: Preparation for Treatment of Psoriasis

Figures 1C, 1D:
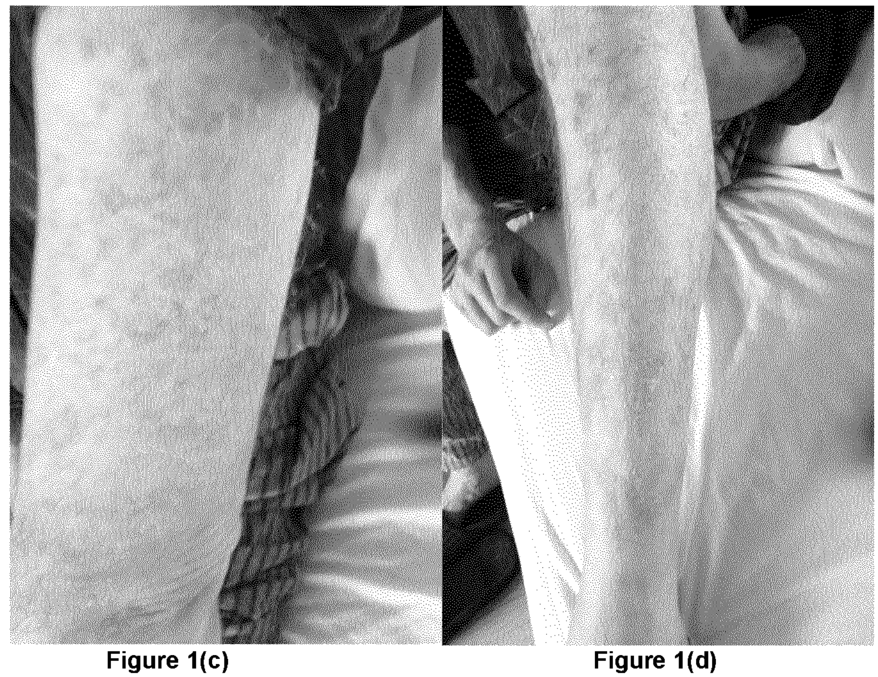

A composition according to the invention (zinc oxide 10%, salicylic acid 2%, iodine 0.01%, aqueous cream 100%) was used to treat psoriasis on the arms and legs of an individual. FIGS. 1(*a*) and 1(*b*) show the arm and leg of the individual on day one of treatment. Throughout the following days of treatments (days two to four) the individual reported a decrease in the propensity to scratch the areas where the composition had been applied, the areas also appeared less inflamed and red to the individual, on day four a decrease in the amount of scaling on the affected areas was evident. FIGS. 1(*c*) and 1(*d*) show the individual's leg and arm on day 7 of treatment. The reduction in inflammation and scaling is apparent.

Example 6: Preparation for Veterinary Treatment of Wounds

Figures 2A, 2B, 2C:
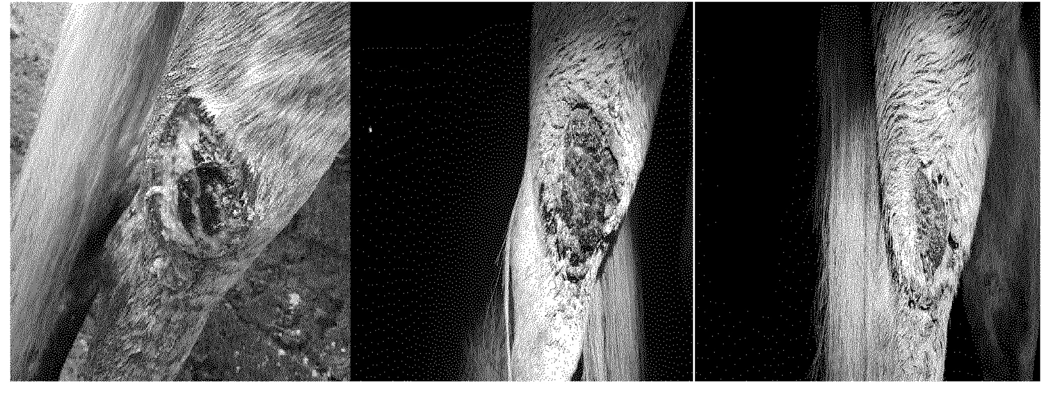
FIGS. 2(*a*) to 2(*e*) illustrate the results of using a preparation in accordance with the invention in the treatment of wounds of the gaskin tissue.
Figures 2D, 2E:
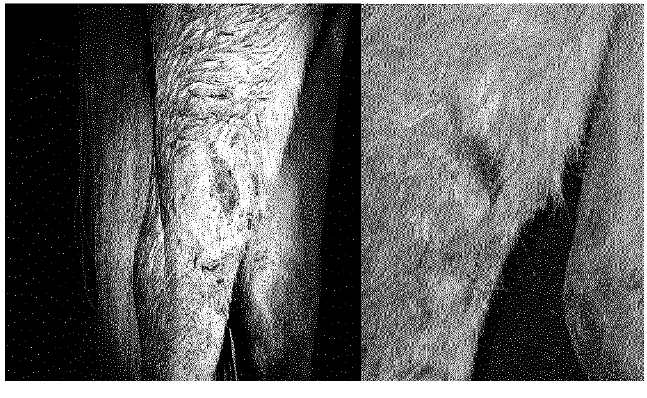
Figures 3A, 3B:
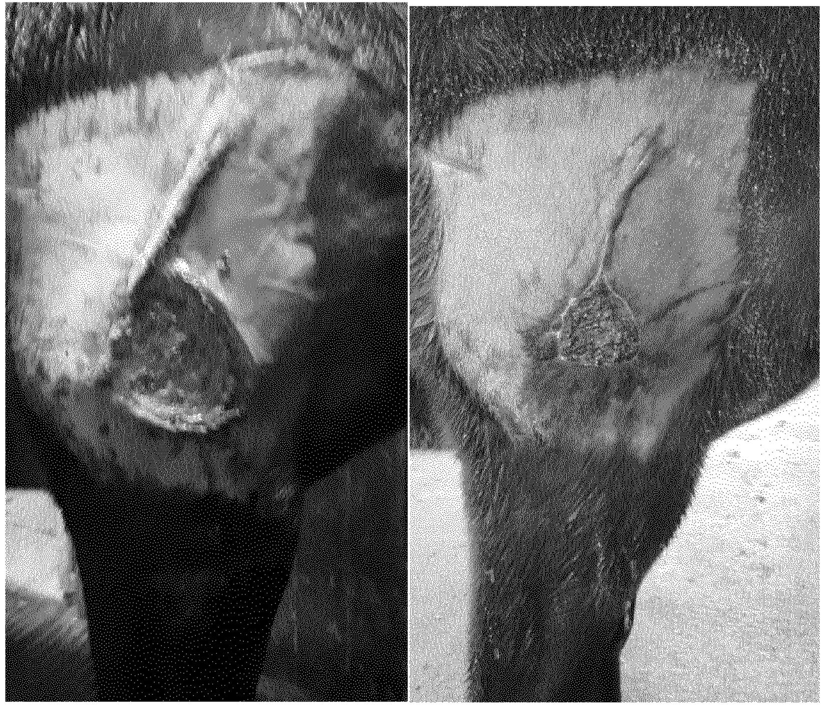
FIGS. 3(*a*) to 3(*g*) illustrate the results of using a preparation in accordance with the invention in the treatment equine wounds arising from a road traffic accident.
Figures 3C, 3D:
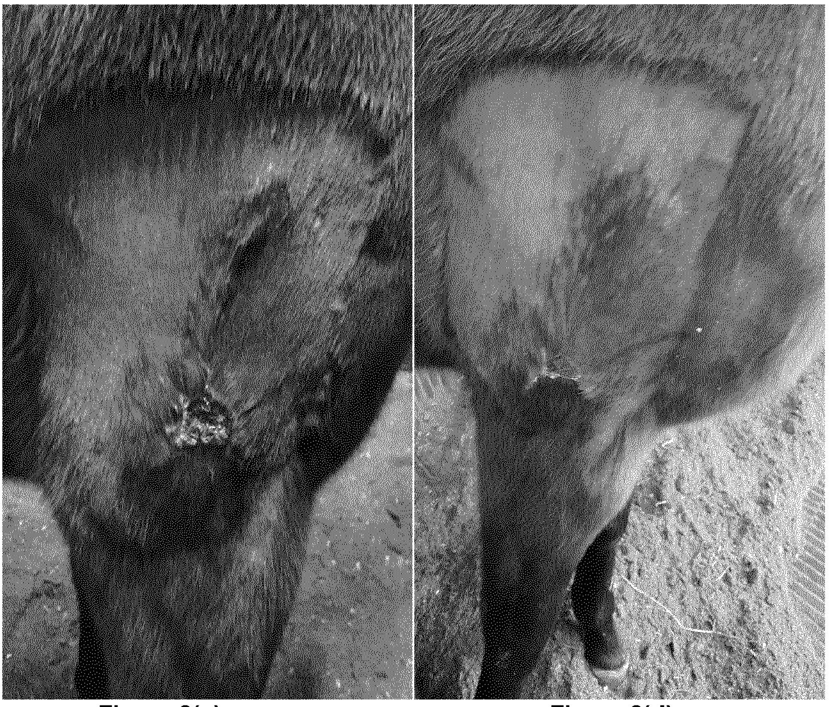
Figures 3E, 3F:
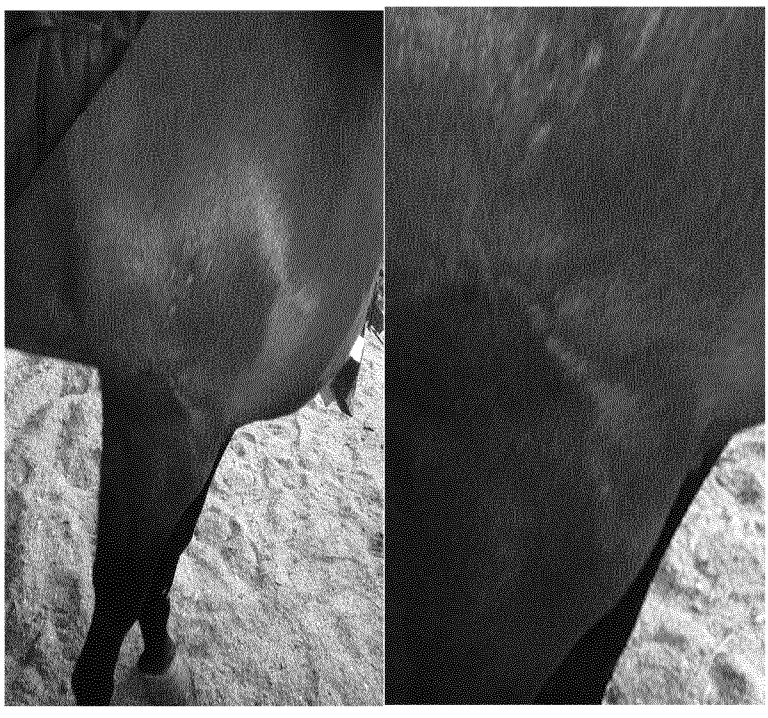
Figure 3G:
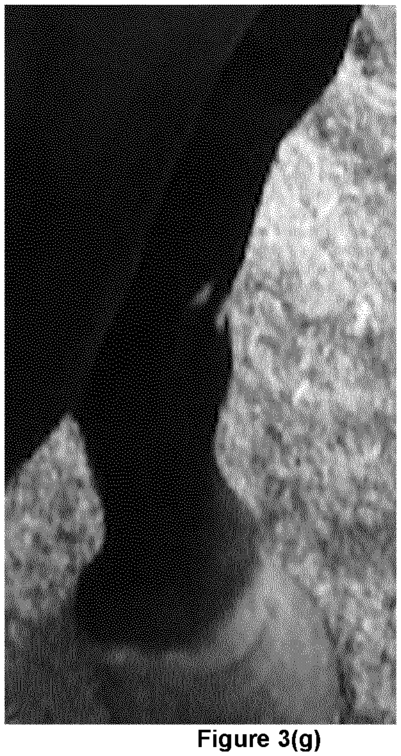
Figure 4A:
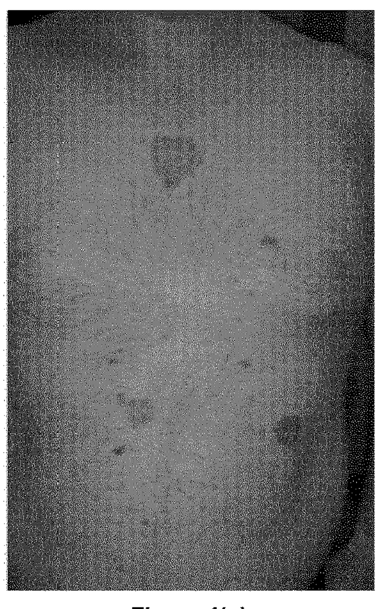
FIGS. 4(*a*) to 4(*g*) illustrate the results of using a preparation in accordance with the invention in the treatment of psoriasis on the human torso.
Figure 4B:
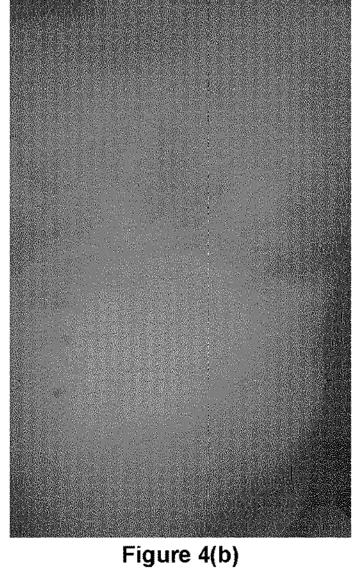
Figure 4C:
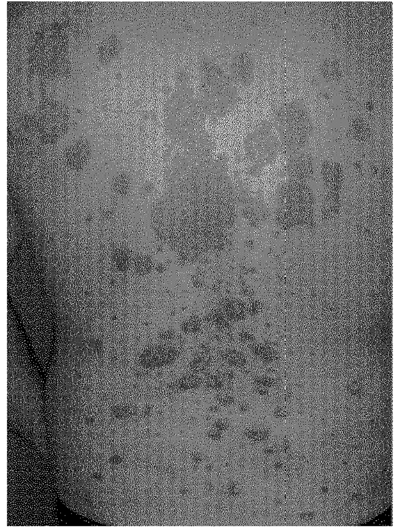
Figure 4D:
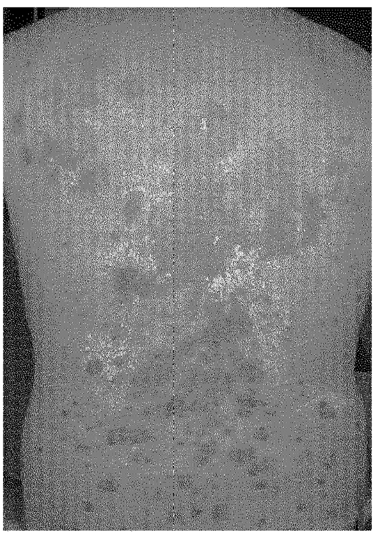
Figure 4E:
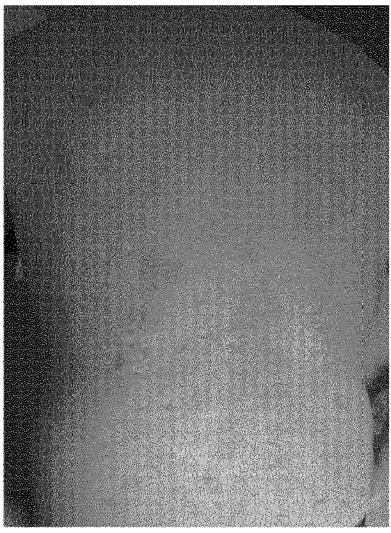
Figure 4F:
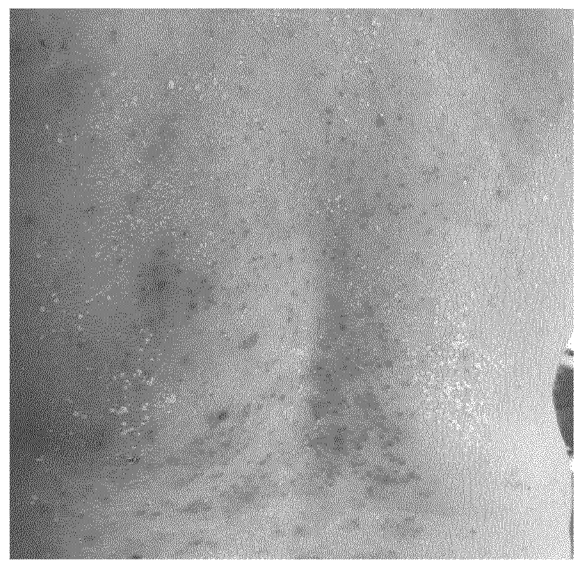
Figure 4G:
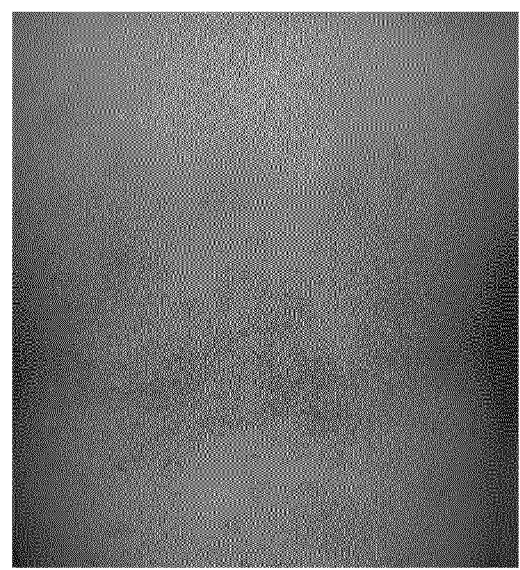
Figure 5A:
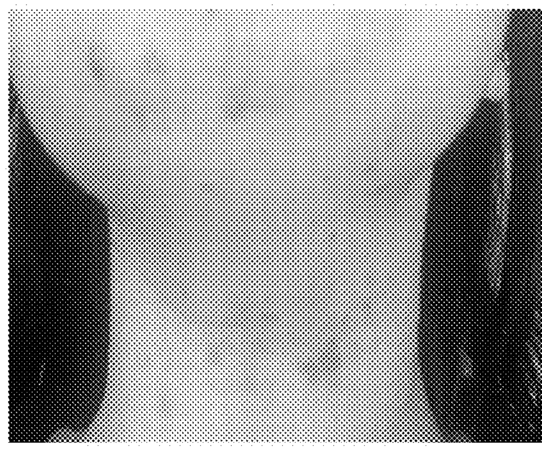
FIGS. 5(*a*) to 5(*h*) illustrate the results of using a preparation in accordance with the invention in the treatment of rosacea.
Figure 5B:
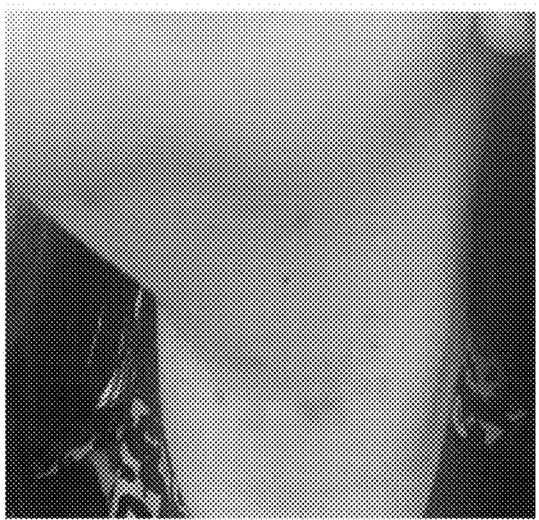
Figure 5C:
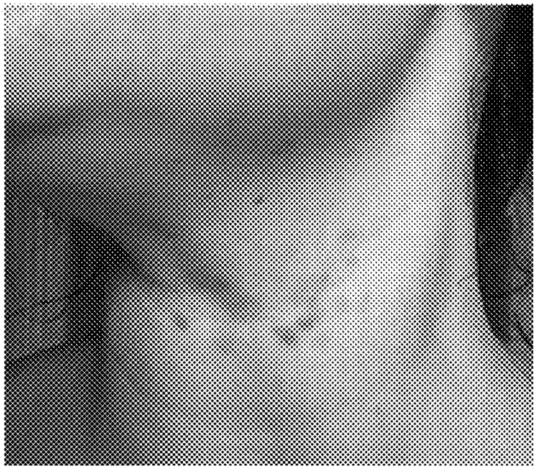
Figure 5D:
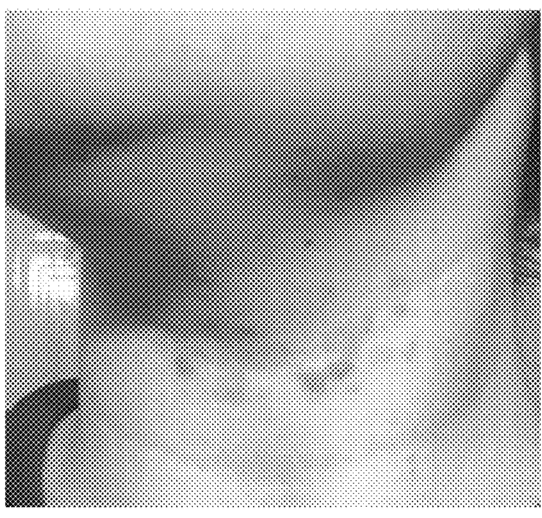
Figure 5E:
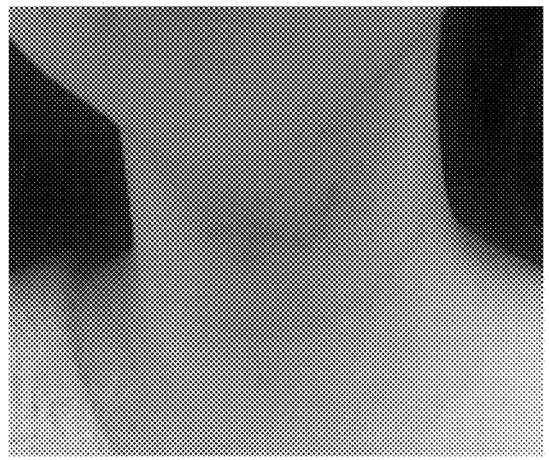
Figure 5G:
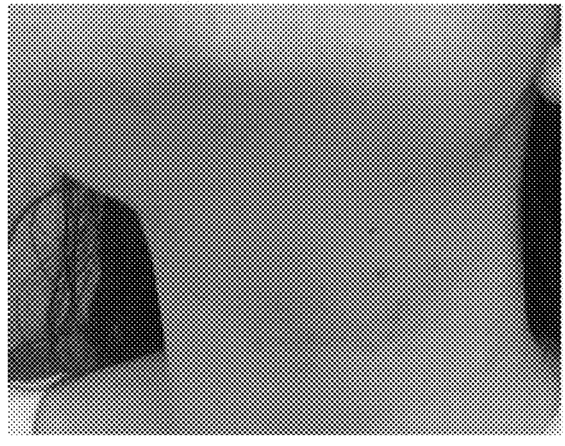
Figure 5H:
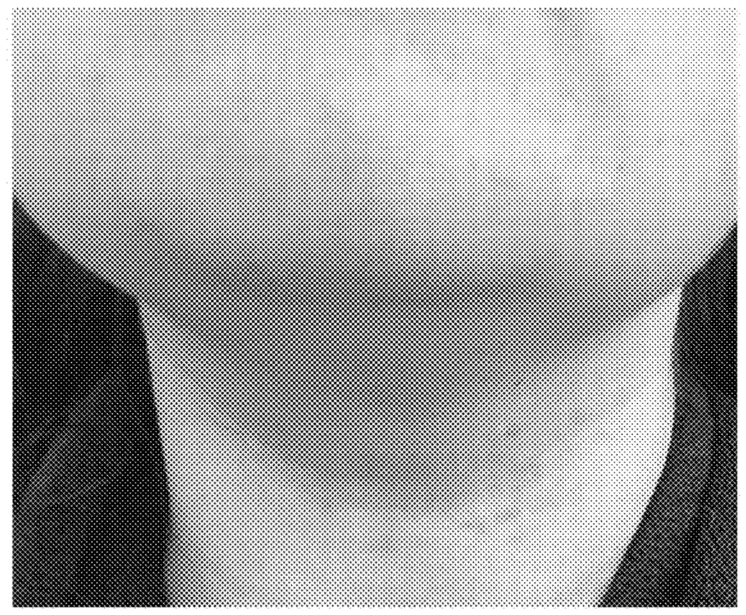

A composition according to the invention (zinc oxide 10%, salicylic acid 2%, iodine 0.01%, aqueous cream to 100%) was used to treat the gaskin tissue of an equine. The gaskin tissue was fully open to the tibia. When the equine walked, the tissue moved relative to the tibia. FIGS. 2(*a*) to 2(*e*) show the different stages of healing with application of the composition. FIG. 2(*a*) shows the open wound on Day 1, FIG. 2(*b*) shows the open wound on day 21 after application of the cream on a daily basis (10 g per application), scabs have started to form, and the wound is red in colour indicating that inflammation is occurring as part of the repair process. FIG. 2(*c*) shows the wound on day 39 of treatment with the composition, the surface area of the wound has significantly decreased, the presence of coagulated blood/scabbing has also decreased. On day 57 the wound size has reduced so significantly it cannot be considered more than a minor cut, see FIG. 2(*d*). The healing is neat and there are no irregularities in the periphery of wound. By day 84 the wound has completely healed as shown in FIG. 2(*e*), it is important to note the hair regeneration that accompanied the wound healing and the complete absence of scarring and granulation tissue. The rapid nature of the healing properties of the cream accelerates post-injury time and consequently for equines competing at a high level, such a composition can reduce time out of competition for the wounded horse and thus is also economically beneficial.

Example 7: Preparation for Veterinary Treatment of Wounds

A composition according to the invention (zinc oxide 10%, salicylic acid 2%, iodine 0.01%, aqueous cream to 100%) was used to treat a very large deep open wound on the shoulder/arm of an equine that occurred as a result of the equine being struck by a lorry. The open wound of FIG. 3(*a*) shows stiches (in blue) at the top of the wound however the surface area of the rest of the wound is too great to permit the application of any further stitches. The veterinary surgeon treating the equine recommended euthanizing as it was not envisaged that the equine would make a recovery whereby the wound would heal to a point where it would not inhibit the equine's normal function. The owner of the equine began treatment with the composition, 10 g of the composition was applied twice daily for forty-five days after which the dosage was reduced to 10 g once daily for twenty-five days. FIG. 3(*b*) shows the wound on day 9 of topical application of the composition. The narrower parts of the wound have already diminished in size leaving only the lower part of the wound open, the strong red colour visible indicates inflammation as such it can be inferred that wound healing is occurring. FIG. 3(*c*) shows day 22 of the use of the composition, the wound has drastically diminished in size and the wound appears to have completely dried up. Day 39 of topical application as show in in the FIG. 3(*d*) shows that the wound has completely healed over, with only minor scabbing remaining and hair regeneration has started to occur. FIG. 3(*e*) shows the wound on day 52 of use of the composition, the wound is barely visible and significant hair regeneration has occurred. FIGS. 3(*f*) and (*g*) show complete hair regeneration and the equine is restored to full health. FIG. 3(*h*) shows a small untreated wound that occurred at the same time, the hair remains grey and elements of proud flesh are present. Overall, the time period for wound healing is sixty days.

Example 8: Preparation for Treatment of Psoriasis

A composition according to the invention (zinc oxide 10%, salicylic acid 2%, iodine 0.01%, aqueous cream to 100%) was used to treat the torso and back of an individual with a severe case of psoriasis for which NSAIDS were ineffective. FIGS. 4(*a*) and 4(*c*) show the individual prior to commencing treatments. The affected area is large, particularly on the back and the affected scaly patches of skin are dark red in colour indicating severe inflammation. The individual commenced a treatment regimen utilizing the composition according to the invention. The regimen involved the topical application of 20 g of the composition twice daily to the affected area over the course of 70 days. FIGS. 4(*d*), 4(*e*) and 4(*f*) show the improvement of the affected areas throughout the treatment. The aforementioned figures show a significant reduction in the size of the affected scaly areas. The colour of the affected area has also improved which indicates a reduction in the level of inflammation. FIGS. 4(*b*) and 4(*g*) show the torso and back of the individual after treatment has finished, the affected areas have decreased significantly in size and there is no evidence of scarring.

Example 9: Preparation for Topical Treatment

A composition according to the invention is prepared for topical application to the epidermis/dermis as follows:

| | |
|---|---|
| Zinc Oxide | 6% |
| Salicylic Acid | 3% |
| Tincture of Iodine | 3% |
| Glyceryl Stearate | 1% |
| Cetyl Alcohol | 1% |
| Xanthan Gum | 0.5% |
| Sucrose Stearate HLB 11 | 1.5% |
| Sucrose Stearate HLB 15 | 4% |
| Castor Oil | 20% |
| Purified water | 60% |

The preparation was prepared according to the following steps:

Castor oil was heated to about 55° C. and glyceryl stearate, cetyl alcohol and xanthan gum were added to the heated oil while stirring and the stirring was continued for five minutes. The purified water was heated to about 45° C. and the iodine tincture then added to the heated water. The solution of iodine in water was then added to the castor oil mix. Zinc oxide and salicylic acid were then added to the mixture while stirring and continued for five minutes. Finally, sucrose stearate HLB 11 and sucrose stearate HLB 15 were added and mixed in a blender for fifteen minutes.

The resulting preparation in the form of a cream displayed excellent stability.

Example 10: Preparation for Treatment of Rosacea

The preparation according to Example 9 was used to treat an individual suffering from rosacea. The preparation in the form of a cream was applied to the face and neck of the individual once daily for the first week, then reduced to one application on each of five days in the second week, and further reduced to one application on two days in the third week.

FIGS. 5(*a*) to 5(*h*) are photographs showing the improvement in the appearance of the skin on the face and neck of the treated individual over the aforementioned three-week period.

Example 11: Preparation for Treatment of "Sweet Itch"

The preparation according to Example 9 was used in late summer to treat several horses suffering from sweet itch. The preparation was applied daily to the horses in the affected areas, especially at the base of the tail, where the constant irritation had resulted in loss of tail hair and open wounds where the flesh had torn. It was observed that all horses treated with the preparation ceased rubbing and scratching from the first day of application, and wound healing was observed from the third day. While it would be usual for horses suffering from sweet itch to have little or no tail hair left at this time in the season, hair regrowth was also observed from as early as the fifth day of treatment. After about one month of treatment, complete hair regrowth was evident even in what would have been considered hopeless cases.

Figure 6A:
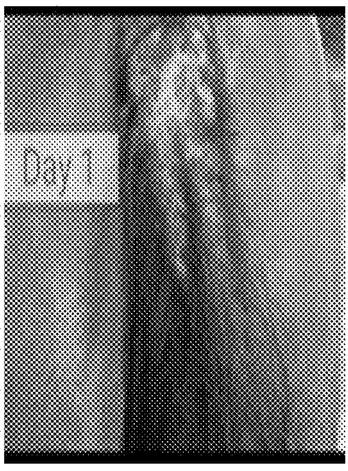
FIGS. 6(*a*) to 6(*c*) illustrate the results of using a preparation in accordance with the invention in the treatment of a horse suffering from “sweet itch”
Figure 6B:
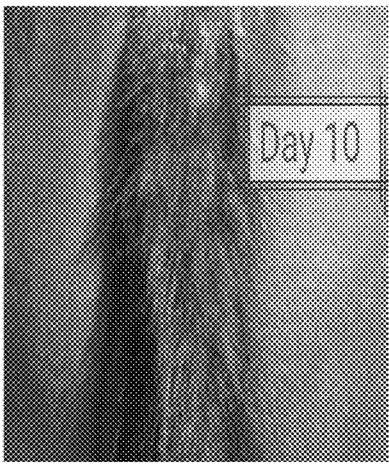
Figure 6C:
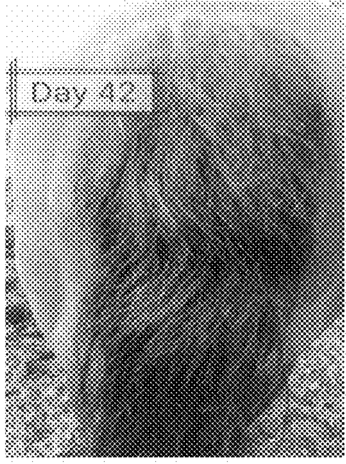

FIGS. 6(*a*) to 6(*c*) are photographs showing the condition of a horse's tail that had been suffering from sweet itch as treatment progressed. As will be seen, after ten days of treatment (FIG. 6(*b*)), the open wounds had substantially healed, and the affected area had almost been completely recovered in tail hair. As evident from FIG. 6(*c*) taken on day 42, the appearance of the tail and tail hair had been completely restored and no visible signs of the condition remained.

Example 12: Preparation for Treatment of Bacterial/Funqal Infection

The preparation according to Example 9 was used to treat an individual suffering from a bacterial/fungal infection across the palm of the hand. The preparation was applied as a cream once daily over a period of two weeks by which time the infection had cleared and the skin had returned to a normal appearance.

Figures 7A, 7B:
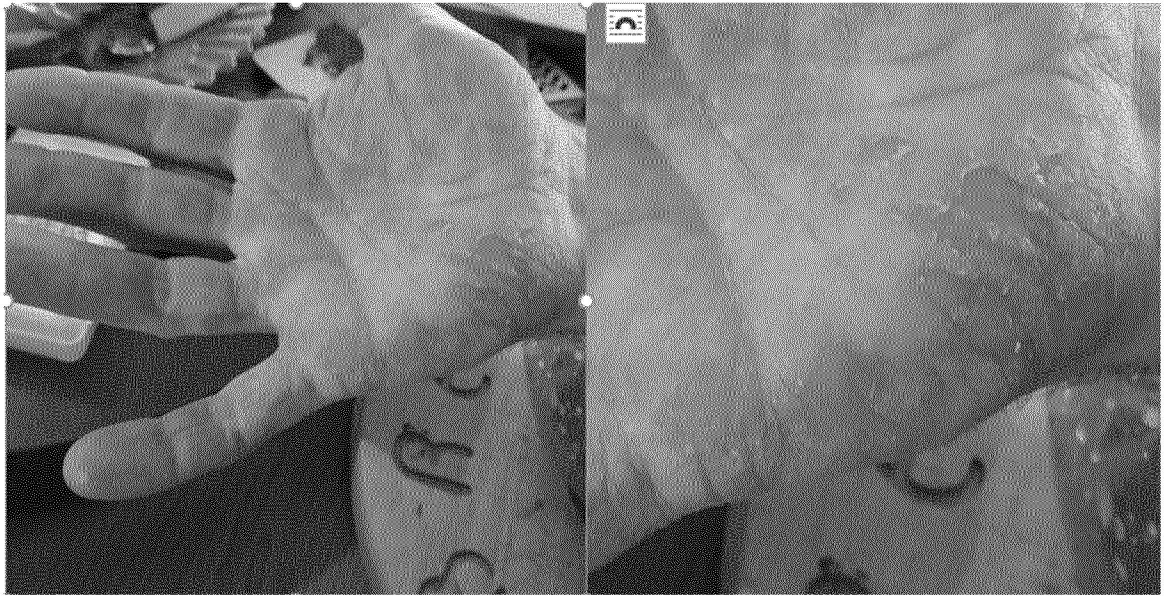
FIGS. 7(*a*) to 7(*d*) illustrate the results of using a preparation in accordance with the invention in the treatment of a bacterial/fungal infection on a hand.
Figures 7C, 7D:
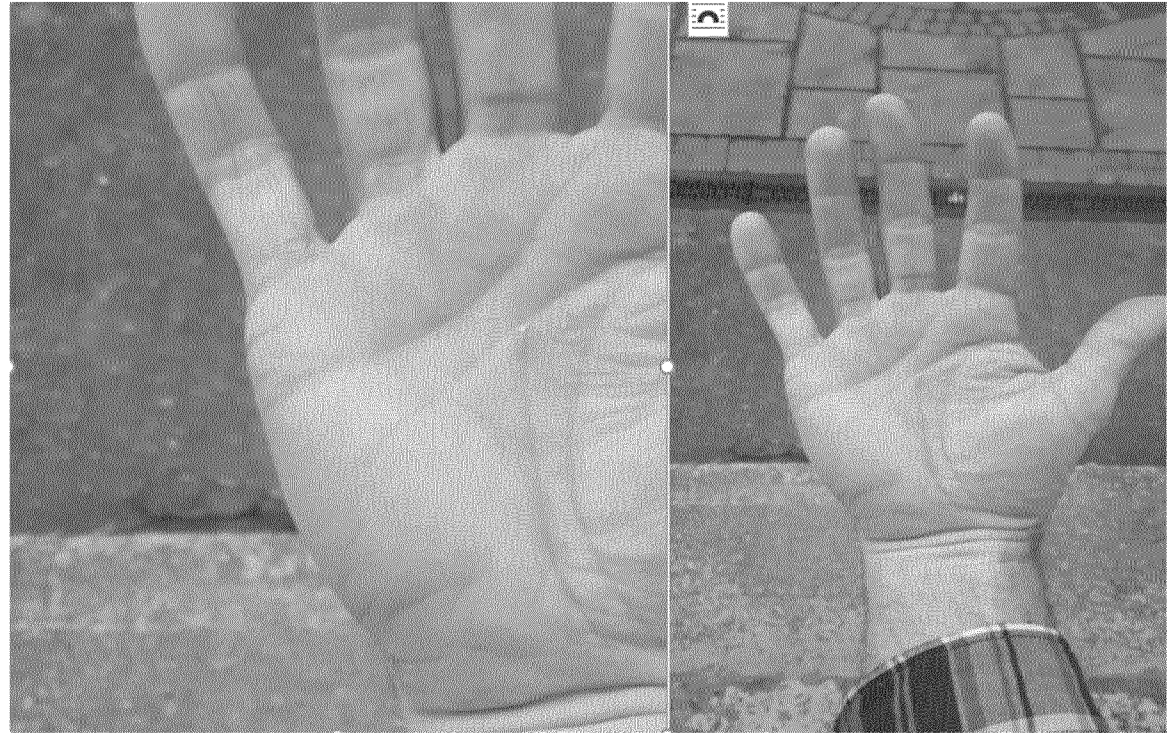

FIGS. 7(*a*) and 7(*b*) show the appearance of the hand before treatment commenced and FIGS. 7(*c*) and 7(*d*) show the transformation following two weeks of treatment.

Example 13: Preparation for Treatment of Infected Equine Wounds

The preparation according to Example 9 was used to treat a horse suffering from lymphangitis that resulted in a severely swollen right hind leg with accompanying pain and elevated temperature. Lymphangitis frequently results in significant permanent scarring of the flesh, and in the present case the leg displayed significant wound swelling as well as a build-up of proud flesh. The horse was initially treated with antibiotics, and subsequently the affected leg area was treated with the preparation which was applied once daily for a period of several weeks.

Recovery visibly commenced within three days from the first application. The preparation eliminated oozing of fluids from the exposed wound and normalized hot spots across the affected area. Further, it was observed that use of the preparation not only accelerated wound healing, but also the existing proud flesh was reduced and indeed substantially eliminated over a three-week period. Regrowth of hair across the affected area was also apparent and ultimately the appearance of the affected leg restored. The horse was able to be returned to its paddock within five weeks of commencing treatment.

Figure 8A:
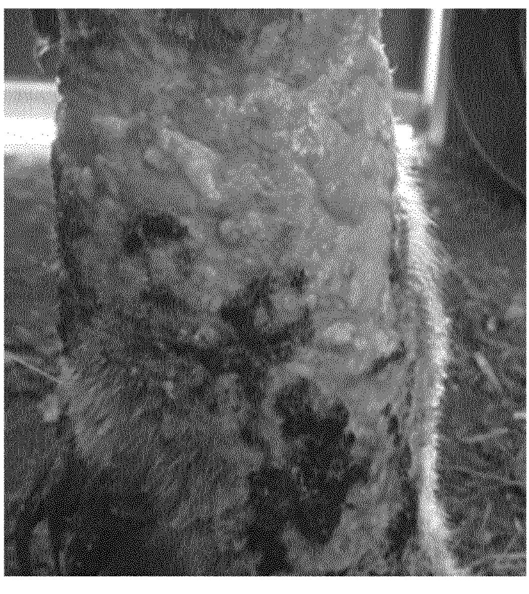
FIGS. 8(*a*) to 8(*d*) illustrate the results of using a preparation in accordance with the invention in the treatment of wounds in a horse suffering from lymphangitis.
Figures 8B, 8C, 8D:
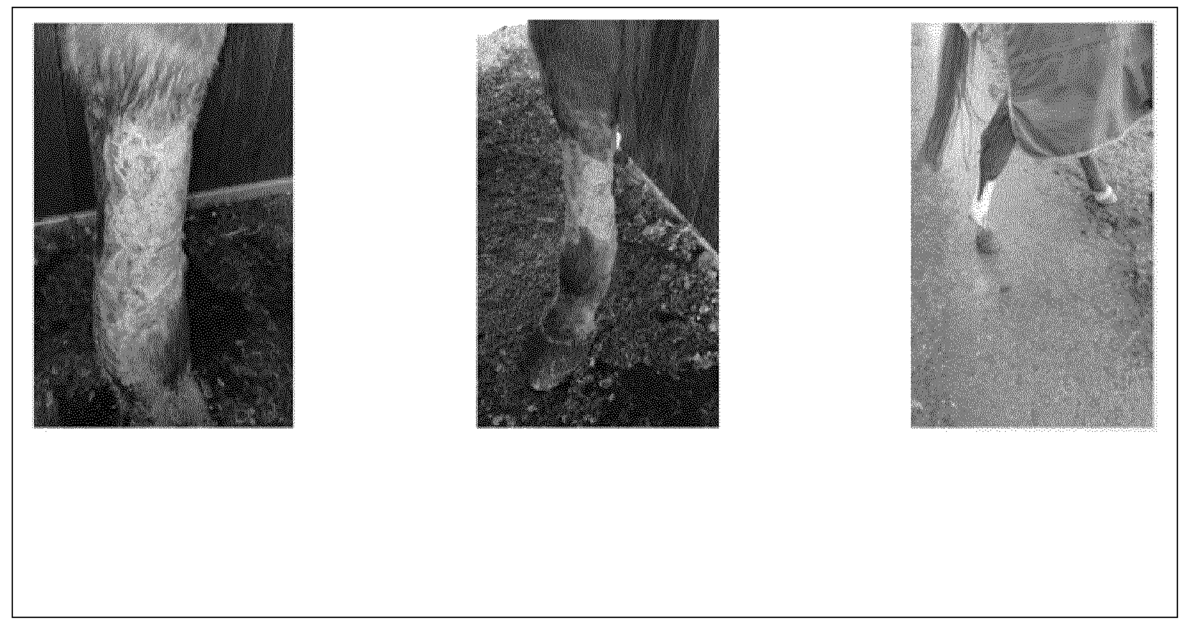

FIGS. 8(*a*) to 8(*d*) show the appearance of the affected hind leg prior to commencement of treatment and the progressive recovery over the five-week treatment period.

Although particular embodiments of the invention have been disclosed herein in detail, this has been done by way of example and for the purposes of illustration only. The aforementioned embodiments and examples are not intended to be limiting with respect to the scope of the appended claims, which follow. It is contemplated by the inventors that various substitutions, alterations, and modifications may be made to the invention without departing from the spirit and scope of the invention as defined by the claims. In addition, the above-described embodiments may be used in combination unless otherwise indicated.

The invention claimed is:

1. A topical preparation for dermatological application, the preparation prepared from a mixture comprising:
- zinc oxide;
- salicylic acid; and
- iodine;
- in a pharmaceutically acceptable carrier vehicle, wherein the mixture comprises salicylic acid in an amount of from 1 to 2% m/m, zinc oxide in an amount of from 5 to 15% m/m, and iodine in an amount of from 0.001 to 0.01% m/m, based on the total mass of the preparation, wherein the iodine is provided in the mixture as a solution in ethanol.

2. The topical preparation according to claim 1, wherein the preparation includes one or more of, zinc iodide, a zinc salicylic acid complex, a zinc iodo-salicylate, an ethyl salicylate, a zinc ethyl salicylate, and/or a zinc ethyl iodo-salicylate.

3. The topical preparation according to claim 1, wherein zinc is present in molar excess with respect to salicylic acid, wherein the molar ratio of zinc to salicylic acid is at least about 1.5:1 and at most 20:1.

4. The topical preparation according to claim 1, wherein salicylic acid is present in molar excess with respect to iodine.

5. The topical preparation according to claim 1, wherein the preparation includes one or more zinc (II) iodo-salicylate.

6. The topical preparation according to claim 1, wherein the preparation includes one or more of zinc salicylate, 3-iodo salicylic acid, 5-iodo salicylic acid, 3,5-di-iodo salicylic acid and/or 3, 4, 5-tri-iodo salicylic acid.

7. The topical preparation according to claim 1, wherein salicylic acid is provided at a concentration of 2% m/m, zinc oxide is provided at a concentration of 10% m/m, and iodine is provided at a concentration of 0.01% m/m.

8. The topical preparation according to claim 1, wherein the carrier vehicle comprises one or more of emulsifying ointment, aqueous cream, castor oil cream, shea butter, hydrogel, alginate hydrogel, liquid paraffin, white soft paraffin, 50/50 liquid paraffin/white soft paraffin or combinations thereof.

9. The topical preparation according to claim 1, wherein the preparation further comprises from 5% m/m to 40% m/m castor oil.

10. The topical preparation for dermatological application according to claim 1, which is in the form of a cream, ointment, paste, lotion, gel, wash, solution, powder or hydrogel.

11. The topical preparation according to claim 1, wherein the pH of the preparation is approximately 5.5 to 6.

12. A method of preparing the topical preparation for dermatological application according to claim 1, said method comprising:
- (a) preparing a mixture of salicylic acid and zinc oxide;
- (b) adding a pharmaceutically acceptable carrier vehicle to the salicylic acid/zinc oxide mixture;
- (c) adding iodine provided as a solution in ethanol to the carrier vehicle/salicylic acid/zinc oxide mixture; and
- (d) agitating the mixture of step (c) to provide a homogenized preparation.

13. The method of claim 12, wherein the salicylic acid/zinc oxide mixture of step (a) is prepared from salicylic acid powder and zinc oxide powder, and the mixture is milled prior to adding the carrier vehicle.

14. A method of preparing the topical preparation for dermatological application according to claim 1, said method comprising:

(a) adding iodine provided as a solution in ethanol to a pharmaceutically acceptable carrier vehicle at a temperature between about 40 to 60° C.;

(b) adding zinc oxide and salicylic acid to the iodine-containing carrier vehicle; and (c) agitating the mixture of step (b) until homogenized.

15. A method of treating a dermatological condition in a subject in need thereof, the method comprising administering to the subject the topical preparation of claim 1.

16. The method according to claim 15, wherein the dermatological condition to be treated is selected from the group consisting of psoriasis, rosacea, SSRD, atopic dermatitis, and a skin wound.

17. The method according to claim 15, wherein the topical preparation is administered daily at a dose of 5 g to 50 g.

18. The method according to claim 15, wherein the topical preparation is administered to the skin of the subject.

19. The method according to claim 15, wherein the subject is a human or an animal.

20. The method according to claim 15, wherein the administering repels biting insects.

21. The method according to claim 12, further comprising adding an additional quantity of pharmaceutically acceptable carrier vehicle to the carrier vehicle/salicylic acid/zinc oxide mixture of step (c) prior to the agitating of step (d).

22. The method according to claim 14, further comprising adding an emulsifier to the mixture of step (b) prior to the agitating of step (c).

* * * * *